United States Patent
Rasnetsov et al.

(10) Patent No.: US 9,221,746 B2
(45) Date of Patent: Dec. 29, 2015

(54) HOMO- AND HETERO-POLYAMINO-ACID DERIVATIVES OF FULLERENE C60, METHOD FOR PRODUCING SAME, AND PHARMACEUTICAL COMPOSITIONS BASED ON SAID DERIVATIVES

(75) Inventors: Lev Davidovich Rasnetsov, Nizhny Novgorod (RU); Iakov Yudelevich Shvartsman, Nizhny Novgorod (RU); Olga Nikolaevna Suvorova, Nizhny Novgorod (RU)

(73) Assignee: RASNETSOV, LEV DAVIDOVICH, Nizhny Novgorod (RU)

( * ) Notice: Subject to any disclaimer, the term of this patent is extended or adjusted under 35 U.S.C. 154(b) by 371 days.

(21) Appl. No.: 13/820,769

(22) PCT Filed: Feb. 6, 2012

(86) PCT No.: PCT/RU2012/000062
§ 371 (c)(1),
(2), (4) Date: Mar. 5, 2013

(87) PCT Pub. No.: WO2012/105872
PCT Pub. Date: Aug. 9, 2012

(65) Prior Publication Data
US 2013/0165691 A1    Jun. 27, 2013

(30) Foreign Application Priority Data
Feb. 1, 2011 (RU) ................. 2011103574

(51) Int. Cl.
| | |
|---|---|
| *C07C 229/14* | (2006.01) |
| *C07C 229/12* | (2006.01) |
| *C07C 229/18* | (2006.01) |
| *C07C 229/08* | (2006.01) |
| *C07C 227/18* | (2006.01) |
| *C07C 237/06* | (2006.01) |

(52) U.S. Cl.
CPC ............ *C07C 229/14* (2013.01); *C07C 227/18* (2013.01); *C07C 229/08* (2013.01); *C07C 229/12* (2013.01); *C07C 237/06* (2013.01); *C07C 2104/00* (2013.01)

(58) Field of Classification Search
CPC   C07C 2104/00; C07C 229/08; C07C 227/18; C07C 237/06
See application file for complete search history.

(56) References Cited

U.S. PATENT DOCUMENTS 6,204,391 B1    3/2001    Friedman et al.

FOREIGN PATENT DOCUMENTS

| RU | 2162819 C2 | 2/2001 |
| RU | 2213048 C1 * | 9/2003 |
| RU | 2236852 C1 | 9/2004 |
| RU | 2316320 C1 | 2/2008 |
| WO | 2009/002203 A1 | 12/2008 |

OTHER PUBLICATIONS

Berge et al, Journal of Pharmaceutical Sciences, Pharmaceutical Salts, 1977, 66(1), pp. 1-19.*
English Abstract RU2236852 C1.
English Abstract RU 2316320 C1.
Bedrov, D., et al., "Passive Transport of $C_{60}$ Fullerenes through a Lipid Membrane: A Molecular Dynamics Simulation Study", J. Phys. Chem. B 200, vol. 112, pp. 2078-2084.
Qiao R., et al., "Translocation of $C_{60}$ and Its Derivatives Across a Lipid Bilayer", Nano Letters 2007, vol. 7, No. 3, pp. 614-619.
Nielsen, G., et al., "In vivo Biology and toxicology of Fullerenes and Their Derivatives", Basic & Clinical Pharmacology & Toxicology, 2008, vol. 103, pp. 197-208.
Kiselev, O, et al., "Antiviral Activity of Fullerene $C_{60}$ with the Poly(N-Vinylpyrrolidone) Complex" Mol. Mat, 1998, vol. 11, pp. 121-124.
Piotrovsky, L., et al., "Study of the Biological Activity of the Adducts of Fullerenes with Poly(N-Vinylpyrrolidone)", Mol. Materials, 2000, vol. 13, pp. 41-50.

* cited by examiner

*Primary Examiner* — Paul A Zucker
(74) *Attorney, Agent, or Firm* — Ladas & Parry LLP

(57) ABSTRACT

The invention relates to the pharmaceutical industry and to medicine, specifically to novel homo- and hetero-polyamino-acid derivatives of fullerene $C_{60}$ of general formula: $C_{60}(H)_x\{NH(CH_2)_nCOO-\}_x\{NH_3^+(L)COOH\}_x$, where n=2-5, x=3, L=-$(CH_2)_m$-, where m=1-5, or —$CO(CH_2)_kCH(NH_2)$—, where k=1-2, characterized in that the compounds comprise covalently bonded amino-acid groups and polar ionic forms of the amino acids, and also to a method for producing said derivatives, and to the production of pharmaceutical compositions based on same. The method for producing homo- and hetero-polyamino-acid derivatives of fullerene is based on the reaction of a nucleophilic bond of amino acids to fullerene, forming covalently bonded amino-acid derivatives of fullerene, with the subsequent introduction of polar ionic forms of the amino acids. A pharmaceutical composition comprises, as active substance, homo- and hetero-polyamino-acid derivatives of fullerene of formula

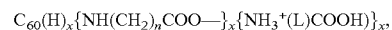

where n=2-5, x=3, L=-$(CH_2)_m$-, where m=1-5, or —$CO(CH_2)_kCH(NH_2)$—, where k=1-2.

7 Claims, No Drawings

HOMO- AND HETERO-POLYAMINO-ACID DERIVATIVES OF FULLERENE C60, METHOD FOR PRODUCING SAME, AND PHARMACEUTICAL COMPOSITIONS BASED ON SAID DERIVATIVES

RELATED APPLICATION INFORMATION

This application is a 371 of International Application PCT/RU2012/000062 filed 6 Feb. 2012 entitled "Homo- And Hetero-Polyamino-Acid Derivatives Of Fullerene $C_{60}$, Method For Producing Same, And Pharmaceutical Compositions Based On Said Derivatives", which was published on 9 Aug. 2012 with International Publication Number WO 2012/105872 AI, and which claims priority from Russian Patent Applications No.: 2011103574 filed 1 Feb. 2011, the contents of which are incorporated herein by reference.

FIELD OF THE ART

This invention relates to the pharmaceutical industry and medicine, namely, to novel homo- and hetero-poly(amino acid) derivatives of fullerene $C_{60}$ of formula (I), and to a method for preparing same and to making pharmaceutical compositions comprising same.

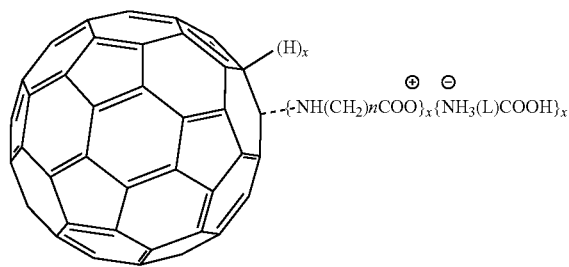

(I)

wherein n=2-5, x=3, L=-$(CH_2)_m$-, when m=2-5 or —CO$(CH_2)_k$CH($NH_2$)—, where k=1-2.

BACKGROUND ART

The medical use of fullerene derivatives is based on the lipophilic properties of the fullerene core, which enables fullerene derivatives to permeate cellular membranes, and the ability of fullerenes to generate in high quantum yield singlet oxygen, which splits DNAs. These properties endow functional fullerene derivatives with cytotoxic, antiviral, and other properties (see Bedrov, D., Smith, G. D., Davande, H., "Passive transport of fullerenes through a lipid membrane," J. Phys. Chem., B, 2008, Vol. 1 12., pp. 2078-84; Qiao, R., and Roberts A. E., "Translocation of fullerene and its derivatives across a lipid bilayer", Nano Lett., 2007, Vol. 7, pp. 614-9; Nelsen, G. D., et al., "In vivo biology and toxicology of fullerenes and their derivatives", Basic and Clinical Pharmacology and Toxicology, 2008, Vol. 103, pp. 197-208; and U.S. Pat. No. 6,204,391, 2005, "Water soluble fullerenes with antiviral activity").

The main problem hampering biological studies of fullerene derivatives and the creation of medicaments on their basis arises from the water insolubility of fullerenes, which hampers their direct administration into a human body. One possible way to overcome these difficulties is to embed fullerene molecules into solubilizing matrices. Methods are known for preparing water-soluble fullerene species through forming a polyvinylpyrrolidone adduct (see Kiselev, O. I., et al., Mol. Materials, 1998, Vol. 11, p. 121; Piotrovsky, L. B., et al., Ibid., 2000, Vol. 13, p. 41). This adduct was shown to be efficient against influenza A and B viruses.

Further, a method is known for preparing fullerenes, which comprises mixing fullerenes pre-dissolved in an organic solvent with a polymeric matrix in chloroform, concentrating the mixture under vacuum until the solvents are completely removed, and dissolving the resulting complex in a phosphate salt buffer (pH 7.4-7.6), followed by an ultrasonic treatment of the product (see RU No. 2162819. Oct. 2, 2001). The water-soluble polymeric matrices used according to that patent are membrane cephalins. The products obtained as a result of such modifications are unstable compositions having limited storage potentials.

A promising method for preparing water-soluble fullerene compositions is offered by chemical modification of the fullerene sphere by incorporation of hydrophilic solubilizing ligands. The international application WO2005/070827 shows a set of amino acid derivatives of fullerene prepared through the cycloaddition reaction of amino acid moieties to fullerene, and the products of their insertion into biologically active organic substrates. The synthesis methods disclosed in that technical solution are multistep and poorly adaptable. The resulting compounds have low water solubilities.

Currently, a wide range of functionalized fullerenes have been prepared, wherein hydrophilic moieties are present in the side chains of ligands attached to the fullerene (the detergent type of complex), as well as spherical derivatives wherein polar groups are distributed over the fullerene sphere (this type includes fullerenols and amino adducts).

Amino acid derivatives of fullerenes have the greatest potential for use.

Analogues of the present invention are the compounds and methods for producing them as described in the international application WO2009/00203 and those described in the Russian Federation patent No. 2236852.

The international application WO2009/00203 described polyfunctional amino acid derivatives of formula

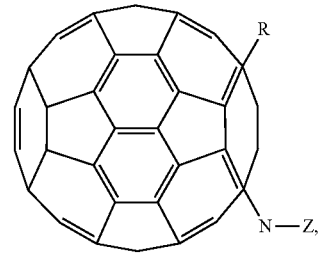

where R=H, mono- or dihydroxyalkyl, haloalkyl, mono- or dinitroxyalkyl, maleinimde; N—Z is a moiety of an α, β, γ, or ω amino acid of general formula —NH—$C_mH_{2m}$—COOM or $C_4H_8N$—COOM, where m=2-5, and M is a nitroxyalkyl group, alkyl group, or an alkali metal salt, or a dipeptide. These compounds were prepared via the reaction of equimolar addition of an amino acid to fullerene, followed by the substitution of a biologically active organic ligand for hydrogen to form the type of compound. The resulting compounds have an inhibitory activity against metastasizing tumors, enhance the antileukemic activity of cyclophosphamide, and can be suitable as nitrogen monoxide donors or as fast acting vasodilators for antihypertensive therapy.

The major drawback of the compounds according to that application consists in that they are covalent addition products, contain small amounts of polar groups, and have low water solubilities.

The most pertinent piece of prior art in the context of the technical essence and the attainable result consists of an agent for inhibiting the reproduction of enveloped viruses and the method of preparing same according to RU patent No. 2236852. As a result of reacting a fullerene with an amino acid salt in an organic solvent in the presence of polyalkylene oxide, fullerene-polycarboxylic anions of general formula $C_{60}H_n[NH(CH_2)_mC(O)O^-]_n$ were prepared, wherein $C_{60}$ is the fullerene core, $NH(CH_2)_mC(O)O^-$ is an aminocarboxylic anion; m is an integer from 1 to 5, and n is an integer from 2 to 12.

In order to prepare these compounds, to a solution of fullerene in o-dichlorobenzene (or toluene or another organic solvent), an amino acid is inserted as a salt (potassium or sodium salt) and then a solubilizing agent is added. The order of addition of the amino acid and solubilizing agent is unimportant; they can be added as a premixed complex. Useful solubilizing agents are various polyalkylene oxides (polyethylene glycols having molar weights from 150 to 400 or higher than 400 (for example, PEG-1500), as well as polyethylene glycol dimethyl ether having a molar weight of 500. In order to increase reaction rates, any strong reducing agent (an alkali metal) is added.

The fullerene-to-amino acid ratio is increased by more than 50 times. Conversion to the desired pharmaceutically acceptable salt, especially, a sodium or potassium salt, was performed by treating the acid with a suitable base or by adding a salt of a weak volatile acid. In particular, a water-insoluble fullerene-polycarboxylic acid is converted to a more preferable pharmaceutically acceptable, water soluble salt, for example to a sodium salt. Addition of a salt of a weak volatile acid is performed via treating the solution with an alkali metal salt of a weak volatile acid. Upon concentrating the solution by evaporation or freeze drying, the weak acid is removed and fullerene-polycarboxylic acids are recovered as their alkali metal salts. The target product of the invention has a constant composition; the content of the major substance in the target product is as low as 87.8%. The specification lacks flowsheet protocols for the determination of optimal amounts of the starting compounds, the ratios of amounts of the solvents used, and most important, the description of methods for isolating the sought compounds.

The major drawbacks of the fullerene amino acid derivatives prepared by the method shown in the cited patent consist of producing a mixture of fullerene-carboxylate anions in the form of both salt and acid species. An individual compound cannot be prepared by the method described in the cited patent. Furthermore, the fullerene poly(amino acids) prepared by this prior-art method in the acid form are almost water insoluble. Attempts at preparing a stable pharmaceutical composition with fullerene-polycarboxylic anions failed, because compounds are precipitating during storage.

The necessity of using in the synthesis of great excesses of a potassium or sodium salt of amino acids and great excesses of solvents gives rise to environmental problems in waste recycling, and increases the cost of the production process. For technological reasons alkali metals cannot be used to increase the reaction rate when chlorinated aromatic solvents are used.

However, the unique biochemical properties of agents comprising fullerene compounds with amino acid moieties described in the cited patent pose the problem of preparing new fullerene derivatives, developing a highly adaptable large-scale process for their production that would be distinguished by simplicity and efficiency, freedom from contaminants, environmental safety, and availability of the starting reagents.

DISCLOSURE OF THE INVENTION

For solving of the above problem, we propose a group of inventions that are linked to each other so as to form a single inventive concept, namely: homo- and hetero-poly(amino acid) derivatives of fullerene, a method for producing fullerene derivatives, and pharmaceutical compositions comprising homo- and hetero-poly(amino acid) derivatives of fullerene as an active agent. Varying reagent ratio and process parameters, one can prepare different fullerene derivatives by the claimed method.

The aforementioned problem is solved by means of homo- and hetero-poly(amino acid) derivatives of fullerene of general formula (II):

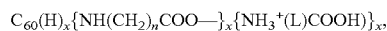

wherein n=2-5, x=3, L=-$(CH_2)_m$, wherein m=1-5, or —$CO(CH_2)_kCH(NH_2)$—, where k=1-2.

When m=n, homopoly(amino acid) derivatives of fullerene are prepared; when m≠n, hetero-poly(amino acid) derivatives of fullerene are prepared.

The problem is solved by the method for preparing homo- and hetero-poly(amino acid) derivatives of fullerene, wherein these derivatives are produced by reacting fullerene with a tenfold excess of anhydrous potassium salts of amino acids in an organic solvent medium with addition of a phase-transfer catalyst to the resulting suspension under stirring and heating to a temperature not higher than 60° C. until the solution is completely decolorized and a solid precipitate is formed to be then separated and again dissolved in water, followed by treating aqueous solutions of potassium salts of fullerene poly(amino acids) with 1 N solution of an organic or mineral acid followed by addition of amino acids solutions in a polar solvent. The method employs freshly prepared anhydrous potassium amino acid salts in a finely dispersed state, and the separation of a solid precipitate of potassium salts of fullerene poly(amino acids) is performed by filtering, ethanol washing, and drying. In the course of experiments it was discovered that fullerene poly(amino acids) of the specified composition can be prepared only when freshly prepared anhydrous potassium amino acid salts are used. Useful phase-transfer catalysts are methyl ethers of polyethylene oxides having molecular weights of 200, 400, or 500.

Another way to solve the problem is to design pharmaceutical compositions wherein the active agents are homo- and hetero-poly(amino acid) derivatives of fullerene of formula (II), which have antiviral activity against herpes, Hepatitis C virus, various influenza viruses, and HIV, and anti-tumor and anti-psoriatic activities. Pharmaceutical compositions can be implemented as tablets, capsules, ointments, emulsions, suppositories, solutions, or sprays.

The pharmaceutical compositions according to the claimed technical solution comprise a compound of general formula (II) in an amount that is efficient to attain the desired result, and can be administered as standard dosage forms (for example, as solid, semisolid, or liquid dosage forms), comprising a compound of the claimed technical solution as an active agent formulated with a carrier or excipient suitable to be administered in the intramuscular, intravenous, oral, sublingual, inhalatory, topical, nasal, rectal, or vaginal route. The active agent can be formulated in the composition together with ordinary nontoxic pharmaceutically acceptable carriers suitable for manufacturing solutions, tablets, pills, capsules, beads, suppositories, emulsions, suspensions, ointments, gels, and other dosage forms.

Particular drug administration levels and periodicity for a particular patient will depend on many factors, including the activity of a particular fullerene derivative, metabolic stability and length of action thereof; excretion rate; patient's age, body weight, general health, and sex; drug combinations; and the severity of the disease in the subject to be treated.

For oral administration in the form of suspensions, the compositions are prepared according to methods well known in the art of preparing pharmaceutical formulations, and they can comprise microcrystalline cellulose or derivatives thereof for providing the desired weight, alginic acid or sodium alginate as a suspending agent, methylcellulose as a viscosity enhancer, and sweetening agents and/or fragrances known in the art. When manufactured in the form of tablets, these compositions can comprise microcrystalline cellulose, calcium phosphate, starch, magnesium stearate, and lactose and/or other excipients, binding agents, expanders, disintegrants, diluents, and lubricants known in the art.

When intended to be administered as nasal aerosols or by inhalation, the compositions are prepared by methods well known in the art of pharmaceutical formulations, and they can be produced as solutions in physiological saline using benzoic acid or other suitable preservatives, adsorption promoters for enhancing bio applicability, and/or other solubilizing or dispersing agents known in the art.

Solutions or suspensions for injections can be formed according to known methods using nontoxic, parenterally applicable diluents or solvents, such as mannitol, 1,3-butanediol, water, Ringer's solution, or isotonic sodium chloride solutions; or suitable dispersing or wetting and suspending agents, such as sterile, soft, and stable oils, including synthetic mono- or diglycerides, or fatty acids, including oleic acid.

When intended to be administered in the rectal or vaginal route in the form of suppositories, the compositions can be prepared by blending a drug with a non-irritating excipient, such as cocoa butter, synthetic glyceride ethers, or polyethylene glycols, which are solid at ordinary temperatures but liquefy and or dissolve in the body cavity to release the drug.

When administered topically in the form of ointments, gels, lotions, liniments, etc., the compositions can be prepared by mixing active ingredients with an acceptable ointment base.

As an ointment base useful are grease, petroleum or hydrophilic bases, such as petrolatum, mineral oil, paraffin, beeswax, lanolin, polyethylene glycol, and others.

As a basis for gels useful are methyl cellulose, sodium carboxymethyl cellulose, oxypropyl cellulose, polyethylene glycol or polyethylene oxide, carbopol, polyvinylpyrrolidone, polyvinyl alcohol, etc.

The technical result of the invention consists in the following: novel homo- and hetero-poly(amino acid) derivatives of fullerene of formula $C_{60}(H)_x\{NH(CH_2)nCOO'\}_x\{NH_3^+(L)COOH)\}_x$, wherein n=2-5, x=3, L=-$(CH_2)_m$, wherein m=1-5, or —$CO(CH_2)_kCH(NH_2)$—, wherein k=1-2, have been prepared, characterized in that the compounds comprise covalently bonded amino acid groups and polar ionic forms of amino acids; a novel large-scale method has been developed for producing amino acid derivatives of fullerene $C_{60}$ with diverse component ratios, using the reaction of nucleophilic addition of the amino acid to the fullerene to form polyaddition products. Pharmaceutical compositions are claimed wherein the active agent is homo- and hetero-poly(amino acid) derivatives of fullerene of formula (II), these derivatives having an antiviral activity against herpes, hepatitis C, various influenza, and HIV viruses and having anti-tumor and anti-psoriatic activities. The pharmaceutical compositions are embodied in the form of tablets, capsules, ointments, suppositories, solutions, and sprays.

The compounds have the following novel properties:
solubility in dimethyl sulfoxide-water (1:100 or 1:200) mixtures;
high bioavailability;
high efficiency in affecting infected cells; and
low toxicity.

The claimed method provides the preparation of diverse homo- and hetero-poly(amino acid) derivatives of fullerene depending on the reagent ratio and process parameters. The underlying idea of the method consists in that it uses, at the synthesis step, optimal reagent ratios (1:10) and minimal amounts of an organic solvent and a phase-transfer catalyst, followed by the recovery of a claimed composition using concentrated solutions of organic and mineral acids, further followed by addition of amino acids of the $NH_2LCOOH$ series, wherein L=-$(CH_2)_m$, or —$CO(CH_2)_kCH(NH_2)$, thereby providing the quantitative production of tailored fullerene amino acid compositions and rendering the claimed method suitable for efficient and environmentally safe large-scale synthesis of these compositions.

The claimed invention will be illustrated by means of examples, which follow.

VARIANT EMBODIMENTS OF THE INVENTION

Example 1

Preparation of Fullerene Poly(Aminocaproic Acid) of Formula $C_{60}(H_3)\{NH(CH_2)_5COO\text{—}\}_3\{NH_3^+(CH_2)_5COOH\}_3$ To a solution of 7.2 g (0.01 mol) of fullerene $C_{60}$ in 400 mL o-dichlorobenzene, added is 17 g (0.1 mol) of a freshly prepared and finely divided anhydrous potassium salt of ε-aminocaproic acid. To the resulting suspension, added is for 2 h under stirring and heating to a temperature not higher than 80° C. a mixture of o-dichlorobenzene and methyl polyethyleneglycol 400 ether in the ratio 2.5:1. The reaction mixture is stirred at a temperature not higher than 60° C. for 2-3 h until the solution completely decolorizes and a solid precipitate is formed. Following this, the mixture is filtered; the precipitate is washed on the filter with several ethanol portions and dried in vacuo a temperature not higher than 60° C. The isolated potassium salt of fullerene amino acid is dissolved in 2 L distilled water. To this solution, 1 N hydrochloric acid is added slowly under stirring until pH becomes 5.1. The mixture is allowed to stand until the product is completely precipitated. Then the aqueous layer is decanted. To the precipitate which is a fine suspension of a solid product in water, a solution of aminocaproic acid in dimethyl sulfoxide/water mixture (1:10) is added slowly under stirring. The mixture is stirred to complete dissolution. Then the solvents are removed by vacuum distillation. A solid residue is dried at a temperature not higher than 60° C. inside a vacuum drier.

The target product yield is quantitative relative to the initial fullerene. The compound is a dark brown solid which is soluble in dimethyl sulfoxide/water (1:200) and incompletely soluble in $CH_3CN:H_2O$ (1:1) and $DMF-H_2O$.

Thermogravimetric analysis of the product shows that the complex contains three moles of weakly bound aminocaproic acid, which are split with decomposition at 200° C. The thermal decomposition of the fullerene poly(amino acid) occurs at 345° C. with the evolution of fullerene and its oxidation products. The amount of the solid residue after the decomposition of the compound, which represents unsubstituted fullerene as shown by X-ray diffraction, corresponds to the ratio $C_{60}$:amino acid moiety of 1:6.

The acid hydrolysis of the compound with 0.1 M HCl solution leads to the release of aminocaproic acid hydrochloride in an amount of 3 moles per mole of the initial substance.

Adsorption of the compound on silica gel brings about splitting of ionic bonds and evolution of free aminocaproic acid. The number of ionically bonded amino acid groups is determined in subsequent photometric analysis of the reaction products of aminocaproic acid with ninhydrin. Their number corresponds with the compositions of the claimed compounds.

The electronic absorbance spectrum of the product does not contain absorption bands from unsubstituted fullerene.

The IR spectrum of the product features absorption bands characteristic of N-substituted amino acids: for —COOH— group, at 1704 $cm^{-1}$ and 1658 $cm^{-1}$; for $NH_3^+$ groups, at 3100, 2550, and 2000 $cm^{-1}$; for —N—H— stretching vibrations, at 3300 $cm^{-1}$; and for N—H— bending vibrations, at 1552 $cm^{-1}$; for $C_{60}$—NH—R—, absorption bands appear at 1104 $cm^{-1}$, 930 $cm^{-1}$, and 830 $cm^{-1}$.

Elemental analysis shows the following element ratios in the product: % C=76.84; % H=4.80; % N=5.15; for the bulk formula $C_{96}H_{75}N_6O_{12}$ (M=1503 g/mol), calcd.: % C=76.49; % H=4.90; % N=5.57.

Example 2

Preparation of N-Fullerene γ-Aminobutyric Acid with β-Alanine of the Formula $C_{60}(H_3)\{NH(CH_2)_3 COO^-\}_3(NH_3^+CH_2—CH_2—COOH)_3$ To a solution of 7.2 g (0.01 mol) of fullerene $C_{60}$ in 400 mL o-dichlorobenzene, added is 14 g (0.1 mol) of a freshly prepared anhydrous potassium salt of γ-aminobutyric acid. To the resulting suspension, added is for 2 h under stirring and heating to a temperature not higher than 60° C. a mixture of o-dichlorobenzene and methyl polyethyleneglycol 400 ether in the ratio 3:1. The reaction mixture is stirred at a temperature not higher than 60° C. for 2-3 h until the solution completely decolorizes and a solid precipitate is formed. Following this, the mixture is filtered; the precipitate is washed on the filter with several ethanol portions and dried in vacuo at a temperature not higher than 60° C. The isolated product is dissolved in distilled water. To this solution, 1 N hydrochloric acid is added slowly under stirring until pH becomes 5.1. The mixture is allowed to stand until the product is precipitated completely. Then, the aqueous layer is decanted. To the precipitate which is a fine suspension of a solid product in water, an ethanolic solution of 2.7 g (0.03 mol) β-alanine is added slowly under stirring. The mixture is stirred for 2 hours until the precipitate dissolves completely. After the solvent is removed, the product (12 g) is isolated.

The compound is a dark brown solid which is soluble in dimethyl sulfoxide/water (1:200) and incompletely soluble in $CH_3CN:H_2O$ (1:1) and DMF-$H_2O$ mixtures.

Thermogravimetric analysis of the product shows that the complex contains three moles of weakly bonded β-alanine, which are split with decomposition at 210° C. The thermal decomposition of the entire complex occurs at 335° C. with the evolution of fullerene in an amount corresponding to the ratio $C_{60}$:amino acid moiety of 1:6

The acid hydrolysis of the resulting compound with 0.01 M HCl solution leads to the release of β-alanine hydrochloride in an amount of 3 moles per mole of the initial substance.

The spectra of the product recorded in dimethyl sulfoxide solutions and in 0.1 N aqueous NaOH feature absorption bands in the region of 217, 260, and 335 nm, which are characteristic of fullerene derivatives, and do not feature absorption bands from free fullerene.

The IR spectrum of the compound features absorption bands characteristic of N-substituted amino acids and the cationic forms of amino acids: for —COOH⁻ group, at 1717 $cm^{-1}$, 1710 $cm^{-1}$, and 1658 $cm^{-1}$; for $NH_3^+$ group, at 3100, 2550, and 2000 $cm^{-1}$; N—H stretching vibrations appear at 3400 $cm^{-1}$; N—H stretching vibrations appear at 3400 $cm^{-1}$; N—H bending vibrations appear at 1552 $cm^{-1}$; and for $C_{60}$—NH—R—, absorption bands appear at 1104 $cm^{-1}$, 930 $cm^{-1}$, and 830 $cm^{-1}$.

Elemental analysis shows the following element ratios in the product: % C=75.24; % H=3.80; % N=6.25; for the bulk formula $C_{81}H_{48}N_6O_{12}$ (M=1296 g/mol), anal. calcd.: % C=75.00, % H=3.70, % N=6.48.

Example 3

Preparation of N-Fullerene ε-Aminocaproic Acid with Glutamine of the Formula $C_{60}(H_3)\{NH(CH_2)_5 COO^-\}_3\{NH_3^+(CO)(CH_2)_2CH(NH_2)COOH\}_3$ The process is carried out in the same manner as in Example 1. The only difference consists of the following: at the step of treating the precipitate after the acidic form of fullerene-aminocaproic acid is precipitated, a solution of 4.5 g glutamine in dimethyl sulfoxide-water is added. The solvents are removed by vacuum distillation.

Elemental analysis shows the following element ratios in the product: % C=71.34; % H=4.80; % N=8.25; for the bulk formula $C_{93}H_{69}N_9O_{15}$ (M=1551 g/mol) calcd.: % C=71.95, % H=4.50, % N=8.12.

The IR spectrum of the product features absorption bands characteristic of N-substituted amino acids and cationic forms of amino acids: for —COOH— group, at 1714 $cm^{-1}$ and 1707 $cm^{-1}$; for —C=O(NH—$C_{60}$), at 1658 $cm^{-1}$; for $NH_3^+$ group, at 3000, 2550, and 2000 $cm^{-1}$; N—H stretching vibrations appear at 3400 $cm^{-1}$; N—H bending vibrations appear at 1552 $cm^{-1}$ and absorption bands of $C_{60}$—NH—R—, at 1104 $cm^{-1}$, 930 $cm^{-1}$, and 830 $cm^{-1}$.

The acid hydrolysis of the compound leads to the release of glutamine hydrochloride in an amount of 3 moles per mole of the initial substance.

The antiviral activity of the compounds was studied against HIV, HSV, and influenza virus; their antitumor activity was also studied. In the examples that follow, the agent prepared by the method described in Example 1 will be referred in the text as agent 1 (fullerene poly(aminocaproic acid)).

Example 4

Anti-HIV Activity Studies of the Fullerene-Poly(Aminocaproic Acid) Agent

These studies were carried out in the Immunodeficiency Viruses Laboratory with the Testing Center on Expert Evaluation of Antiviral Agents and Disinfectants (Ivanovsky Research Institute for Virology, Russian Academy of Medicinal Sciences).

Cells were added with the test formulation and infected with the virus in a dose of 0.01 $TCD_{50}$/cell. Cell cultures were incubated at 37° C. under a 5% $CO_2$ atmosphere and 98% humidity for 4 to 5 days. The results were ascertained by staining the cells with a dye and by optical microscopy: studies of the cytopathic effect (CPE) of the virus and virus-induced syncytium formation (syncytium is a conglomerate of several cells having an all-enclosing cell membrane formed through membrane fusion).

The degree of cytodestruction was assessed under the microscope according to the commonly accepted four-plus system using "+" and "−" symbols depending on the number of dead cells in each of the four wells corresponding to one test parameter.

++++ means the 100% death of cells in the four wells used in a single-dilution test;

+++ means the 75% death of cells in the four wells;

++ means the 50% death of cells in each of the four wells;

+ means the 25% death of cells in each of the four wells;

+− means the onset degeneration; and

− means the absence of cytodestruction.

The results of these studies are displayed in Tables 1 and 2.

These results (see Tables 1 and 2) show that the fullerene poly(aminocaproic acid) samples studied have an antiviral activity against the type 1 human immunodeficiency virus. The $EC_{50}$ (50% effective concentration) of the sample is 0.9 mcg/mL. In concentrations of 0.5 to 10 mcg/mL, the agent has no cytotoxic effect on cells.

Example 5

In Vitro Experimental Studies of the Anti-Herpetic Activity of the Fullerene Poly(Aminocaproic Acid) Agent These studies were performed at the Evanovsky Research Institute for Virology, Russian Academy of Medicinal Sciences, Moscow.

The subject of the study was the cytotoxic and anti-herpetic activity of the agent in Vero cell cultures.

In the study there were used: transplantable monkey kidney cell culture (VERO), purchased from the Tissue Culture Collection of the Ivanovsky Research Institute for Virology, Russian Academy of Medicinal Sciences; and Herpes simplex virus, type 1, Lg strain propagated in Vero cells. The cells were infected with the virus in a dose of 100 $TCD_{50}/0.2$ mL and 1000 $TCD_{50}/0.2$ mL.

The test sample of the substance used was a dark-colored powder.

The sample was initially dissolved in dimethyl sulfoxide (DMSO) in the proportion 1:20, and then working concentrations were prepared in the IGLA MEM medium. The activities of the test samples were assessed as the degree of protection of cells from the virus-induced cytotoxic effect of HSV using a microscopic method and the MTT assay as optical density.

Results of the studies. The toxicity of the substances in the concentrations used and the toxicity of the solvent (1.5 mL DMSO in 50 mL water) were studied.

The agent in final concentrations of from 50 to 1000 mcg/mL was added to a VERO cell culture monolayer and incubated in a 5.0% CO2 atmosphere at 37° C. for 24 to 48 hours. The cell monolayer was stained with a 0.4% Trypan Blue solution and then inspected under a microscope.

The sample did not cause a toxic effect on the VERO cell culture when used in concentrations of up to 100 mcg/mL; when the concentration was 200 mcg/mL, signatures of toxic effect appeared: the cell death rate was 25%. Concentrations of 500 mcg/mL or higher are toxic for Vero cells (Table 3).

The protective properties of the sample were studied in one administration scheme, namely, one hour prior to infection and with two virus doses (100 $TCD_{50}$ and 1000 $TCD_{50}$).

The results are displayed in Tables 3 to 7. The above-described studies show that the administration of the agent 60 minutes prior to infecting a cell culture with Herpes simplex virus in a dose of 100 $TCD_{50}$ completely protects the cells from the cytodestructive effect of the virus for all of the concentrations tested, which were from 5.0 mcg/mL and higher (see Tables 4 and 5).

When the infecting Herpes virus dose increased to 1000 $TCD_{50}/0.2$ mL (see Tables 6 and 7), the agent sample provides the complete protection of a sensitive cell culture from the cytodestructive effect of the virus in the chosen test scheme (wherein cells are infected with the virus 60 minutes post inserting the agent into the culture medium).

Example 6

Antiviral Activity Studies of Fullerene Poly(Aminocaproic Acid) (Agent No. 1) Against the A/IIV-Moscow/01/2009 (H1N1)swl Influenza Virus These studies were carried out at the Ivanovsky Research Institute for Virology, Russian Academy of Medicinal Sciences, Moscow. The task was to study the antiviral activity of these agents in MDCK cell culture against the A/IIV-Moscow/01/2009(H1N1)swl influenza virus.

The agent was diluted with DMSO (5 mg substance+0.5 mL DMSO), followed by addition of 4.5 mL MEM cell cultural medium to obtain in this way a stock solution with a concentration of 1.0 мГ/mL. Subsequently, the stocks were diluted with the MEM medium to obtain the following series of working concentrations: 6.5 mcg/mL-12.5-25.0-50.0-100 mcg/mL.

The antiviral activity was ascertained from the reduction of influenza virus reproduction in the MDCK cell culture, as recognized by ELISA.

For this purpose, MDCK cells were grown on 96-well plates to obtain a complete monolayer, washed from the growth medium, and added with substances in a twofold concentration in 100 mcL MEM medium. Infection with the virus in a working dose ranging from 100 to 1000 $TCD_{50}$ was carried out in two protocols: 2 hours following the insertion of the substances and simultaneously. The plates were incubated in a thermostat filled with $CO_2$ for 24 hours at 37° C. Following the incubation, the medium was removed and cells were fixed by 80% acetone in PBS for 15 minutes and then well dried, and ELISA was performed by consecutive adsorption of specific reagents, namely, monoclonal antibodies, conjugate, and substrate (orthophenylenediamine). The degree of reaction was monitored by measuring optical density at 492 nM on a Biokom spectrophotometer. Each virus dilution was studied in three replicas, for which an average optical density (OD) value was calculated. Percent inhibition was determined as the quotient of the difference between the experimental OD and the OD of the cell control, divided by the difference between the OD of the virus control and the OD of the cell control, multiplied by 100%. The data gained in this way were used to determine the minimal concentration of the agent causing the 50.0% inhibition of viral reproduction ($MIC_{50}$).

The inhibition of A(H1N1) influenza virus replication was ascertained in three experiments with different multiplicities of infection. The results are displayed in Table 8 (as protocols of the three experiments) and in Table 9 (as average results of the three experiments).

One can see from Table 9 that there is a clear-cut correlation between the degree of reproduction and the concentration of the agent: as the concentration increases, virus reproduction decreases. Further, there is no noticeable difference in values regardless of the infection protocol (2 hours post insertion of the agent or simultaneously).

Thus, the activity results obtained for different dilutions of the agent against the A/IIV-Moscow/01/2009 (H1N1)swl influenza virus demonstrate a high reproduction inhibitory activity in the MDCK cell culture. The agent insertion protocol (2 h prior to infection or simultaneously with infecting) does not affect the activity of the agent in the MDCK cell culture.

Example No. 7

Antiviral Activity Studies of Fullerene Poly(Aminocaproic Acid) (Agent No. 1) on Induced Influenza Pneumonia in Mice These studies were performed at the Medicinal Chemistry Center (TsKhLS-VNIKhFI), Moscow.

The agent used in the studies was in the form of a dark-brown crystalline powder. The doses of the agent required for oral administration were prepared by dissolving weighed portions in a 1% starch solution cooked with water. For intraperitoneal or intramuscular administration, weighed portions of the agent were dissolved in 1.5% DMSO solution.

The virus used was mouse-adapted A/Aichi/2/69 (H3N2) influenza virus. This virus is widely used to determine the efficiency of antiviral agents in induced influenza pneumonia in mice and was purchased from the Museum of Viral Strains and Cell Cultures of the Ivanovsky Research Institute for Virology, Russian Academy of Medicinal Sciences. In order to prepare the infecting material, mice were infected intranasally with the allantoic virus; once symptoms of the disease developed, the mice were killed and a lung tissue homogenate was prepared under sterile conditions. Then, this homogenate was used to infect 10-day chicken embryos, from which the allantoic virus was derived to be used, after titrating it in mice, to infect animals.

White non-pedigree (female) mice having body weights of 12 to 14 g were purchased from the Andreevka nursery (Moscow oblast) and maintained on a standard ration in regulated vivarium conditions.

Pre-weighed mice (nonlinear female mice with average body weights of 12 to 14 g) were infected intranasally under light ether anesthesia with the A/Aichi/2/69 (H3N2) influenza virus (10 $LD_{50}$ in 100 mcL). The $LD_{50}$ was determined in a preliminary experiment by titrating the allantoic virus in the same mice that were then used in the major experiment. The treatment scheme with the test agent was as follows: 24 hours prior to infection, 1 hours prior to infection, 24 post infection, and then once a day in 24 hours for 5 days. For oral administration, an insulin syringe with a special needle (lavage) was used; each dose was administered in an amount of 100 mcL. For intraperitoneal and intramuscular administration, each dose was also injected in an amount of 100 mcL. The virus control group was comprised of 10 mice that were infected with the virus but not treated by agents. In the experiment there were also two groups of 10 uninfected mice each, each mouse receiving intraperitoneally and intramuscularly 100 mcL of 1.5% DMSO, which was used as the solvent for agents. The other groups were also each initially comprised of 10 animals. The treated and control animals were monitored daily; in the first five days post infection, the mice were weighed every day, and then every next day. The chemotherapeutic activity of the agent in induced influenza pneumonia was ascertained by three criteria, namely: percent protection from deadly viral infection, an increase in average lifetime, and a decrease in body weight loss in groups of animals treated with the agent, compared to the control group.

Treatment with fullerene aminocaproic acid was efficient in decreasing the death rate from influenza pneumonia in mice and weight loss thereof and increasing the average lifetime compared to the virus control. The efficiency of this treatment depended on the dose of the agent and the treatment scheme. The results are displayed in Tables 10 and 11.

Intramuscular treatment with fullerene poly(aminocaproic acid) was most efficient in terms of all of the three parameters (percent death protection, average lifetime, and weight loss); when administered in doses of 100 and 200 mg/kg/day, this treatment prevented the death of 60 to 70% of the infected animals and weight loss in them, and also increased their lifetime almost twofold. Intraperitoneal treatment with fullerene poly(aminocaproic acid) was efficient only in doses of 50 and 100 mg/kg/day. The death rate, a considerable reduction in average lifetime and in body weight in mice upon intraperitoneal treatment thereof with fullerene poly(aminocaproic acid) in a dose of 200 mg/kg/day imply that this dose with this treatment method is toxic for infected mice.

Example No. 8

Antitumor Activity Studies of Fullerene Poly(Aminocaproic Acid) (Agent No. 1) in Transplantable L1210 Leukosis, Breast Adenocarcinoma Ca-755, and Lewis Carcinoma Tumors These studies were carried out at the Institute for Toxicology, St. Petersburg, 2006, according to "Guidelines for the Study of Antitumor Activity of Pharmacological Agents" ("Manual on Experimental (Preclinical) Study of New Pharmacological Agents," Ministry of Public Health of the Russian Federation, Remedium, Moscow, 2000, pp. 319-325).

The L1210 leukemia, breast adenocarcinoma Ca-755, and Lewis carcinoma (3LL) tumor cell strain were purchased from the Petrov Research Institute for Oncology, the Ministry of Public Health of the Russian Federation (St. Petersburg).

These studies employed the following test systems:

DBA/2 line mice with transplanted L1210 leukemia cells. Mouse ages: 6 to 8 weeks; body weights: 19 to 25 g.

C 57 BL/6J line male mice with transplanted Ca-755 cells. Mouse ages: 6 to 8 weeks; body weights: 19 to 25 g.

C 57 BL/6J line male mice with transplanted 3LL cells. Mouse ages: 6 to 8 weeks; body weights: 18 to 24 g.

The antitumor effect was ascertained through the following parameters:

ascite accumulation as animal body weight gain;

the lifetime of animals; and tumor growth. The larger dimension of the tumor (length) and the smaller dimension normal thereto (width) were measured. The tumor volume was calculated, and the inhibition of tumor growth was calculated by a formula. The ascertainment criterion was the day when each individual tumor reached a volume of 500 $mm^3$.

The results on the effect of the agent on the development of L1210 leukemia are displayed in Table 12.

Table 13 displays average lifetimes in animals with transplantable tumors of L1210 leukemia and the control group, as well as the increase in lifetime compared to the control group in percent.

One can see from Table 13 that the average lifetime in the control group mice with transplanted L1210 leukemia cells was 6.0±0.21 days. The administration of the agent reliably increased lifetimes in mice to 10.7±0.37 days and 10.60±0.37 days. The percent increase in lifetime compared to the control was 78.33% and 76.67% for agent doses of 100 mg/kg and 200 mg/kg, respectively; however, differences between the experimental groups appeared statistically unreliable.

During the experiment, the animals were weighed daily with the goal of evaluating ascite accumulation and studying the agents compared on this process.

The results of body weight gain evaluations are displayed in Table 14. One can see from Table 14 that the tested agent reliably reduced ascite accumulation in mice with transplanted L1210 leukemia tumors. The body weight gain in mice that received the tested agent was reliably lower than in the control group; moreover, in the animals that received the tested agent in a dose of 250 mg/kg, the average body weight gain was reliably (by a factor of 1.5) lower than the same parameter in the animals that received the agent in a dose of 100 mg/kg.

Thus, the above results imply that the agent has a well-defined antitumor activity and inhibits L1210 leukemia tumor growth in mice, which is manifested in the reliable increase in lifetime (78.33% and 76.67%) for doses of 100 and 250 mg/kg, respectively, and in a reliable inhibition of ascite accumulation in experimental animals (78 to 43%). No intoxication signatures were detected on the background of the administration of the tested agent. An inspection of the results shows reliable differences between a dose of 100 mg/kg and a dose of 250 mg/kg: the increase in dose of the agent leads to a reliable decrease in ascite accumulation in experimental animals.

For the other parameters, the contrast (the difference of averages for the groups that earlier received different doses of the test agent) was at the level of errors caused by natural variance.

The results on the effect of the agent on the development of breast adenocarcinoma Ca-755 are displayed in Table 15.

Table 16 displays average lifetimes in animals with transplantable breast adenocarcinoma Ca-755 tumors and the control group animals, as well as the increase in lifetime compared to the control group, in percent.

One can see from Table 16 that the average lifetime in the control group mice with transplanted breast adenocarcinoma Ca-755 tumor cells was 37.9+0.74 days. The administration of the agent reliably increased the lifetime in mice to 71.9±2.58 days and 73.4+0.92 days; the percent increase in lifetime compared to the control was 89.71% and 93.67% for doses of the agent of 100 mg/kg and 200 mg/kg, respectively; however, the differences between experimental groups appeared statistically unreliable.

Thus, the above results imply that the agent has a pronounced antitumor effect and inhibits the growth of tumor cells of breast adenocarcinoma Ca-755 in mice, which was manifested as a reliable increase in lifetime (89.71% and 93.67%) for doses of 100 and 250 mg/kg. No intoxication signatures were detected on the background of the administration of the tested agent.

The effect of the agent on the average volume of Lewis carcinoma tumors was ascertained in different days after transplantation. In the control group, tumors developed in 21 of the 26 mice (80.8%); the first tumors appeared on day 7 post transplantation and were observed up to day 40. The first tumors in the group affected by the agent in a dose of 100 mg/kg were observed on day 7 post transplantation and observed up to day 60; in the group affected by the agent in a dose of 250 mg/kg, they appeared on day 8 post transplantation and were observed up to day 60. The agent had a prominent antitumor effect on the development of Lewis lung carcinoma; the percent inhibition in the group affected by the agent in a dose of 100 mg/kg on day 10 to day 17 was reliably 71.77% and 58.5% compared to the control group; in the group affected by the agent in a dose of 250 mg/kg compared to the control group, percent inhibition on day 10 to day 17—84.37% was and 54.2%, respectively.

Table 17 displays the effect of the agent on growth of Lewis lung carcinoma; the parameters analyzed were timeframes for the tumor to achieve a size of 500 $mm^3$; in the control group, this parameter ranged from 12 to 20 days, and in experimental groups, from 17 to 28 days. As one can see from this table, the agent reliably increased this parameter by 22 to 27% compared to the control.

In the control group mice, death occurred as a result of progressing tumor growth of the main focus, and due to extensive metastatic lesion of the lung. Individual lifetimes in the control group mice ranged from 28 to 39 days; in the groups where the mice received the agent, from 51 to 60 days. Table 18 displays the effect of the agent on the average lifetime in mice following tumor transplantation. On can see from Table 18 that the agent reliably increased the average lifetime by approximately 70% against the control group; the difference between test groups is statistically unreliable.

Individual values of the weight of lungs and the number of metastases in lungs in mice of the control group and in the mice of the test groups that received the agents under comparison, are displayed in Table 19.

One can see from Table 19 that the agent reliably decreased the weight of lungs and the number of metastases in lungs by a factor of 1.5 to 2. The difference between the test groups is statistically unreliable.

TABLE 1

Cytotoxicity of the agent studied in human lymphoblastoid cells model

| Run parameters, concentration, mcg/mL | | Cell survival rate, % | Number of cells × $10^3$/mL |
|---|---|---|---|
| Cell control | | 98 | 800 |
| Agent No. 1 | 0.5 | 95 | 833 |
| | 1.0 | 94 | 833 |
| | 5.0 | 98 | 799 |
| | 10.0 | 94 | 767 |
| | 100 | 95 | 600 |

TABLE 2

Antiviral activity of the agent studied on HIV-1 infected human cell model

| Run parameters | Concentration, mcg/mL | Cell survival rate, % | Number of cells × $10^3$/mL | CPE/ syncytia (+) |
|---|---|---|---|---|
| Cell control | 0 | 98 | 800 | 0 |
| Virus control | 0 | 20 | 66 | 4.0 |
| Agent No. 1 | 0.5 | 18 | 33 | 4.0 |
| | 1.0 | 26 | 495 | 4.0 |
| | 5.0 | 98 | 633 | 0 |
| | 10 | 98 | 600 | 0 |

TABLE 3

Cytotoxic effect of a fullerene poly(aminocaproic acid) sample on the Vero cell culture

| Concentration of the agent, Mcg/mL | Cytotoxic effect on cells, % |
|---|---|
| 50 | 0.0 |
| 100 | 0.0 |
| 200 | 25.0 |
| 500 | 100.0 |
| 1000 | 100.0 |

Note:
DMSO in the concentration used for dissolution does not cause a cytotoxic effect on cells.

TABLE 4

Anti-herpetic activity of a fullerene poly(aminocaproic acid) sample in the Vero cell culture with an infecting Herpes virus dose of 100 $TCD_{50}/0.2$ mL

| Concentration of the agent, mcg/mL | Protection of cells from the cytotoxic effect of the Herpes virus, % |
|---|---|
| 5.0 | 81.25 ± 12.5 |
| 10.0 | 100 ± 0.0 |
| 50.0 | 100 ± 0.0 |
| 100.0 | 100 ± 0.0 |

Note:
Cells were infected one hour post insertion of the sample.

TABLE 5

Protective effect of the agent against the destructive effect of Type 1 Herpes virus for an infecting virus dose of 100 $TCD_{50}$

| | Agent No. 1 | |
|---|---|---|
| Concentration of the agent, mcg/mL | Optical density | Difference from the control is reliable for p |
| 0 | 0.403 ± 0.02 | |
| 5.0 | 1.110 ± 0.08 | <0.01 |
| 10.0 | 1.015 ± 0.07 | <0.01 |
| 50.0 | 1.153 ± 0.06 | <0.01 |
| 100.0 | 1.79 ± 0.05 | <0.01 |
| Cell control | 1.133 ± 0.07 | <0.01 |

TABLE 6

Anti-herpetic activity of a fullerene poly(aminocaproic acid) sample in the Vero cell culture with an infecting Herpes virus dose of 1000 $TCD_{50}/0.2$ mL

| Concentration of the agent, mcg/mL | Protection of cells from the cytotoxic effect of the Herpes virus, % |
|---|---|
| 5.0 | 100 ± 0.0 |
| 10.0 | 100 ± 0.0 |
| 50.0 | 100 ± 0.0 |
| 100.0 | 100 ± 0.0 |

Note:
The cells were infected one hour post insertion of the sample.

TABLE 7

Protective effect of agent No. 1 against the cytopathic action of the type 1 Herpes virus with an infecting Herpes virus dose of 1000 $TCD_{50}$

| Concentration of the agent, mcg/mL | Optical density | Difference from control is reliable for P |
|---|---|---|
| 0 | 0.796 ± 0.06 | |
| 5.0 | 1.027 ± 0.04 | <0.01 |
| 10.0 | 1.021 ± 0.04 | <0.01 |
| 50.0 | 1.033 ± 0.03 | <0.01 |
| 100.0 | 1.083 ± 0.01 | <0.01 |
| Cell control | 1.133 ± 0.07 | |

TABLE 8

Activity values of agent No. 1 against influenza virus A/IIV-Moscow/01/2009 (H1N1)swl

| Concentration of the agent (mcg/mL) | Administration protocol | Percent (%) reduction of influenza virus reproduction in MDCK cell culture relative to control in the presence of the series of agent No. 1 |
|---|---|---|
| 6.25 | 2 h prior to infection | 27.0-28.0-0 |
| | simultaneously with infection | 18.0-0-0 |
| 12.5 | 2 h prior to infection | 47.0-74.0-9.5 |
| | simultaneously with infection | 39.0-13.0-0 |
| 25.0 | 2 h prior to infection | 41.0-79.0-12 |
| | simultaneously with infection | 40.0-0 |
| 50.0 | 2 h prior to infection | 28.0-72.0-31.0 |
| | simultaneously with infection | 33.0-10.0 |
| 100.0 | 2 h prior to infection | 4.0-0-20.0 |
| | simultaneously with infection | 29.0-28.0 |

The differences between the values of the two runs depended on the viral infection multiplicity of the MDCK cell culture.

The differences between the values of the two runs depended on the viral infection multiplicity of the MDCK cell culture.

TABLE 9

Activity values of agents against influenza virus A/IIV-Moscow/01/2009 (H1N1)swl, average values

| Concentration of the agent (mcg/mL) | Administration protocol | Percent reduction of influenza virus reproduction in MDCK cell culture relative to control in the presence of series of agent No. 1 |
|---|---|---|
| 6.25 | 2 h prior to infection | 18.0 |
| | simultaneously with infection | 6.0 |
| 12.5 | 2 h prior to infection | 44.0 |
| | simultaneously with infection | 26 |
| 25.0 | 2 h prior to infection | 44.0 |
| | simultaneously with infection | 20.0 |
| 50.0 | 2 h prior to infection | 44.0 |
| | simultaneously with infection | 22.0 |
| 100.0 | 2 h prior to infection | 8 |
| | simultaneously with infection | 29.0 |

TABLE 10

Efficiency of fullerene poly(aminocaproic acid) in induced influenza infection in mice

| | LD70* | | LD90** | |
|---|---|---|---|---|
| Dose of the agent | Percent death protection (%) | Average lifetime (days)** | Percent death protection (%) | Average lifetime (days)* |
| Fullerene poly(amino acid), orally | | | | |
| 100 mg/kg/day | 40 | 13.1 (1-8 d., 1-10 d., 1-11 d.) | 30 | 10.8 (2-7 d., 1-9 d., 2-10 d., 1-11 d) |
| 200 mg/kg/day | 70 | >16 | 60 | 13.4 (1-10 d., 2-11 d) |
| 300 mg/kg/day | 40 | 12.8 (1-8 d., 2-9 d.) | Not studied | Not studied |
| Fullerene (polyamino acid), intramuscularly | | | | |
| 50 mg/kg/day | 50 | 13.3 (1-7 d., 1-8 d.) | 40 | 11.4 (2-7 d., 1-8 d., 2-11 d) |
| 100 mg/kg/day 200 mg/kg/day | 70 | >16 | 60 | 13.0 (1-8 d., 1-9 d., 1-11 d.) |
| 1.5% DMSO solution | 50 | 13.8 (1-7 d., 1-13 d.) >16 | 60 | 13.1 (1-7 d., 2-11 d) >16 |
| Fullerene (polyamino acid), intraperitoneally | | | | |
| 50 mg/kg/day 100 mg/kg/day | 50 | 13.4 (2-8 d.) | 40 | 11.5 (2-7 d. D-9 d., 2-11 d.) |
| 200 mg/kg/day | 60 | 13.7 (1-3 d.) | 30 | 10 D3-7 d., 2-8 d., 1-9 d.) |
| 1.5% DMSO solution | 0 | 3.1 (3-1 d., 1-2 d., 2-3 d., 1-5 d., 1-8 d.) >16 | Not studied | Not studied >16 |
| Virus Control (10 LD$_{50}$) | | 10.1 (4-8 d., 2-10 d., 1-11 d.) | | 7.3 (5-7 d., 4-8 d) |

Notes:
*In experiments the death rate in the virus control group was 70%; that is, seven of the 10 mice died.
**In experiments the death rate in the virus control group was 90%; that is, nine of the ten mice died.
*Treatment scheme: 24 hours and 1 hour prior to infection, then in 24, 48, 72, and 96 hours post infection.

TABLE 11

Weight change in animals infected with influenza virus A/Aichi/2/69 (dose LD70) and treated with agents

| | Percent body weight change in days post infection | | | | | | | | |
|---|---|---|---|---|---|---|---|---|---|
| Dose of the agent | day 1 | day 2 | day 3 | day 4 | day 5 | day 7 | day 9 | day 11 | day 13 |
| Fullerene poly(amino acid), orally | | | | | | | | | |
| 100 mg/kg/day | +19 | +23 | +25 | +22 | +16 | +17 | +24 | +43 | +51 |
| 200 mg/kg/day | +26 | +31 | +36 | +36 | +36 | +38 | +47 | +51 | +57 |
| 300 mg/kg/day | +24 | +27 | +28 | +24 | +19 | +23 | +35 | +36 | +38 |
| Fullerene poly(amino acid), intramuscularly | | | | | | | | | |
| 50 mg/kg/day | +20 | +22 | +22 | +17 | +11 | +9 | +11 | +19 | +26 |
| 100 mg/kg/day | +21 | +25 | +27 | +23 | +20 | +21.5 | +32 | +35.5 | +38 |
| 200 mg/kg/day | +25 | +27 | +28 | +24 | +20 | +23 | +22 | +25 | +36.5 |
| Fullerene poly(amino acid), intraperitoneally | | | | | | | | | |
| 50 mg/kg/day | +21 | +27 | +29 | +21 | +16 | +15 | +31 | +36 | +40 |
| 100 mg/kg/day | +19 | +23 | +22 | +18 | +15 | +18 | +25 | +33 | +41 |
| 200 mg/kg/day | +7 | +6 | +5 | −4 | −3 | −7 | +4 | +6 | +15 |
| Virus Control | +19 | +24 | +31 | +9 | +0.9 | −11 | +4 | +27 | +37 |

TABLE 12

Effect of the agent on the lifetime in mice with transplantable L1210 leukemia tumor

| | Animal No. and its lifetime in days | | | | | | | | | |
|---|---|---|---|---|---|---|---|---|---|---|
| Name of group | 1 | 2 | 3 | 4 | 5 | 6 | 7 | 8 | 9 | 10 |
| Control | 6 | 7 | 7 | 6 | 6 | 5 | 6 | 6 | 5 | 6 |
| Agent No. 1, 100 mg/kg | 9 | 11 | 13 | 11 | 12 | 10 | 11 | 10 | 10 | 10 |
| Agent No. 1, 250 mg/kg | 10 | 10 | 10 | 9 | 10 | 11 | 13 | 10 | 11 | 12 |

TABLE 13

Effect of the agent on the average lifetime in animals with transplantable L1210 leukemia tumor

| Name of group | ALT in days, M ± m | ILT, % |
|---|---|---|
| Control | 6.0 ± 0.21 | |
| Agent No. 1, 100 mg/kg | 10.7 ± 37* | 78.33 |
| Agent No. 1, 250 mg/kg | 10.60 ± 37* | 76.67 |

Note:
*Reliable difference from control (for $p < 0.05$).

TABLE 14

Effect of the agent on ascite development in mice with transplantable L1210 leukemia tumor

| | Control Group | Agent 100 mg/kg | | Agent 250 mg/kg | |
|---|---|---|---|---|---|
| Day | Average body weight gain, M ± m | Average body weight gain, M ± m | Percent inhibition relative to control | Average weight gain, M ± m | Percent inhibition relative to control |
| 1 | 0.4 + 0.2 | 0.3 ± 0.2 | | 0.3 ± 0.1 | |
| 2 | 0.9 ± 0.3 | 0.8 ± 0.4 | | 0.5 ± 0.3 | |
| 3 | 5.0 ± 0.8 | 2.5 ± 0.5 | 50.0%* | 1.1 ± 0.4 | 78.0%* |
| 4 | 11.4 ± 1.1 | 4.2 ± 1.0 | 63.2%* | 2.8 ± 0.9 | 75.4%* |
| 5 | 16.3 ± 2.0 | 8.4 ± 1.2 | 48.5%* | 4.7 ± 1.2 | 71.2%* |
| 6 | 21.2 ± 2.1 | 12.1 ± 2.1 | 42.9%* | 8.4 ± 1.6 | 60.4%* |
| 7 | 26.3 ± 1.7 | 14.2 ± 2.2 | 46.0%* | 10.0 ± 1.3 | 62.0%* |

Note:
*Reliable difference from control (for $p < 0.05$).

TABLE 15

Effect of the agent on the lifetime in mice with transplantable leukemia tumor CA-755

| | Animal No. and its lifetime in days | | | | | | | | | |
|---|---|---|---|---|---|---|---|---|---|---|
| Name of group | 1 | 2 | 3 | 4 | 5 | 6 | 7 | 8 | 9 | 10 |
| Control | 36 | 39 | 41 | 34 | 35 | 40 | 39 | 38 | 40 | 37 |
| Agent No. 1, 100 mg/kg | 79 | 81 | 73 | 82 | 80 | 66 | 63 | 60 | 67 | 68 |
| Agent No. 1, 250 mg/kg | 77 | 72 | 70 | 78 | 76 | 71 | 73 | 70 | 72 | 75 |

TABLE 16

Effect of the agent on the average lifetime in animals with transplantable breast adenocarcinoma tumor Ca-755

| Name of group | ALT in days, M ± m | ILT, % |
|---|---|---|
| Control | 37.9 ± 0.74 | |
| Agent No. 1, 100 mg/kg | 71.9 ± 2.58* | 89.71 |
| Agent No. 1, 250 mg/kg | 73.40 ± 0.92* | 93.67 |

Note:
*Reliable difference from control (for $p < 0.05$).

TABLE 17

Effect of the agent on Lewis carcinoma size (attainment of V = 10 500 mm³)

| | Day when the tumor achieves a volume of 500 mm | |
|---|---|---|
| Group | M ± m | Percent increase, statistical significance |
| Control | 16.7 ± 0.65 | |
| Agent No. 1, 100 mg/kg | 21.3 ± 1.21 | 27.3%* |
| Agent No. 1, 250 mg/kg | 20.5 ± 1.20 | 22.9%* |

Note:
*Reliable difference from control (for $p < 0.05$).

TABLE 18

Effect of the agent on the lifetime in mice after transplantation of Lewis carcinoma

| | Lifetime | |
|---|---|---|
| Group | M ± m | Percent increase, statistical significance |
| Control | 32.81 ± 0.86 | |
| Agent 100 mg/kg | 55.92 ± 0.98 | 70.42%* |
| Agent 250 mg/kg | 56.38 ± 0.68 | 71.85%* |

Note:
*Reliable difference from control (for $p < 0.05$).

TABLE 19

Effect of the agent on Lewis carcinoma metastasizing in mice

| Group No. (number of animals) | Weight of lungs, mg M + m | Number of metastases in lungs, M ± m | Number of large (>3 mm) metastases in lungs, M ± m |
|---|---|---|---|
| Control (n = 21) | 1486.7 ± 64.08 | 70.5 ± 5.50 | 13.4 ± 2.05 |
| Agent No. 1, 100 mg/kg (n = 12) | 491.9 ± 63.72* | 53.5 ± 11.23* | 5.8 ± 1.91* |
| Agent No. 1, 250 mg/kg (n = 13) | 505.4 ± 68.82* | 55.8 ± 11.60* | 5.7 ± 1.54* |

Note:
*Reliable difference from control (for $p < 0.05$).

The invention claimed is:

1. A homo- or hetero-poly(amino acid) derivative of fullerene, the derivative comprising amino acid groups covalently bonded to $C_{60}$ and being of the general formula:

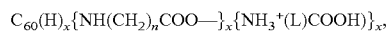

$$C_{60}(H)_x\{NH(CH_2)_nCOO-\}_x\{NH_3^+(L)COOH\}_x,$$

wherein n=2-5, x=3, L=-$(CH_2)_m$, wherein m=1-5, or —CO$(CH_2)_k$CH$(NH_2)$—, wherein k=1-2.

2. The fullerene derivative according to claim 1, wherein the amino acid groups comprise a moiety of an aliphatic amino acid of general formula NH$(CH_2)_n$COOH, wherein n=2-5.

3. Fullerene derivatives according to claim 1, wherein the amino acid groups comprise a moiety of a dicarboxylic amino acid amide of general formula NH$_2$(CO)$(CH_2)_k$CH(NH$_2$)COOH, wherein k=1-2.

4. A method for producing the fullerene derivatives according to claim 1, comprising reacting fullerene with a tenfold molar excess of anhydrous potassium salts of amino acids of general formula NH$_2$(CH$_2$)$_n$COOK, wherein n=2-5, in an aromatic organic solvent medium to form a suspension, addition to the suspension of a phase-transfer catalyst under stirring and heating to a temperature not higher than 60-80° C. to form a completely decolorized solution and a solid precipitate of potassium salts of fullerene poly(amino acids), said precipitate being then separated and dissolved in water to form an aqueous solution of potassium salts of fullerene poly (amino acids), which is then treated with a 1 N solution of organic or mineral acid followed by addition of a solution, in polar solvents, of an amino acid of general formula NH$_2$(L)COOH, wherein L=-$(CH_2)_m$, where m=1-5, or —CO$(CH_2)_k$CH(NH$_2$)—, wherein k=1-2, stirring, removing solvents, washing, and drying a resulting precipitate.

5. The method according to claim 4, wherein the anhydrous potassium salts of amino acids are in a finely dispersed state and the potassium salts of fullerene poly(amino acids) are separated by filtering, ethanol washing, and drying.

6. The method according to claim 4, wherein the phase-transfer catalyst is a methyl polyethylene oxide ether having a molecular weight of 200, 400, or 500.

7. A pharmaceutical composition comprising the fullerene derivative according to claim 1 and a pharmaceutically acceptable carrier or excipient.

* * * * *